US00PP29690P2

(12) United States Plant Patent
Danziger

(10) Patent No.: US PP29,690 P2
(45) Date of Patent: Sep. 18, 2018

(54) ***GYPSOPHILA* PLANT NAMED 'DGYPXLMU'**

(50) Latin Name: *Gypsophila paniculata*
Varietal Denomination: DGYPXLMU

(71) Applicant: Gavriel Danziger, Beit Dagan (IL)

(72) Inventor: Gavriel Danziger, Beit Dagan (IL)

(73) Assignee: Danziger 'DAN' Flower Farm (IL)

( * ) Notice: Subject to any disclaimer, the term of this patent is extended or adjusted under 35 U.S.C. 154(b) by 0 days.

(21) Appl. No.: 15/530,978

(22) Filed: Mar. 30, 2017

(51) Int. Cl.
*A01H 5/02* (2018.01)

(52) U.S. Cl.
USPC ..... Plt./354
CPC ..... *A01H 5/02* (2013.01)

(58) Field of Classification Search
USPC ..... Plt./354
CPC ..... A01H 5/02
See application file for complete search history.

*Primary Examiner* — Kent L Bell
(74) *Attorney, Agent, or Firm* — Cassandra Bright

(57) ABSTRACT

A new and distinct *Gypsophila* cultivar named 'DGYPXLMU' is disclosed, characterized by medium flower size, medium plant size and early flowering. The new variety is a *Gypsophila*, suitable for cut flower production and outdoor garden or container uses.

2 Drawing Sheets

Latin name of the genus and species: *Gypsophila paniculata.*
Variety denomination: 'DGYPXLMU'.

BACKGROUND OF THE INVENTION

The new *Gypsophila* cultivar is a product of chance discovery by the inventor, Gavriel Danziger. The new variety was discovered growing in a commercial field of the commercial variety 'DGYPXLENCE' in Ecuador during June 2013. The parent variety is the propriety variety referred to as *Gypsophila* 'DGYPXLENCE', unpatented in the United States and protected under Plant Breeder's Rights in Brazil, Columbia, Ecuador, the European Union, Guatemala, Israel, Japan, Kenya, Mexico and South Korea.

Asexual reproduction of the new cultivar 'DGYPXLMU' was first performed by basal vegetative cuttings during January 2014, at a greenhouse in Ecuador. Subsequent propagation has shown that the unique features of this cultivar are stable and reproduced true to type in multiple successive generations.

SUMMARY OF THE INVENTION

The cultivar 'DGYPXLMU' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DGYPXLMU' These characteristics in combination distinguish 'DGYPXLMU' as a new and distinct *Gypsophila* cultivar:

1. Medium flower diameter.
2. Medium plant height.
3. Early flowering.

PARENT COMPARISON

Plants of the new cultivar 'DGYPXLMU' are similar to plants of the parent, in most horticultural characteristics, however, plants of the new cultivar 'DGYPXLMU' differ in the following;

1. Flower size of the new variety is smaller than that of the parent.
2. Plants of the new variety are shorter than plants of the parent.
3. Stems of the new variety are stronger than stems of the parent.
4. Branching angle of the new variety is more narrow than that of the parent variety.

COMMERCIAL COMPARISON

Plants of the new cultivar 'DGYPXLMU' can be compared to the commercial variety *Gypsophila* 'DDGYPBRIDE', unpatented in the United States, protected under Plant Breeders' rights in the European Union, Brazil, Colombia, Ecuador, Mexico and South Korea. The varieties are similar in most horticultural characteristics; however, 'DGYPXLMU' differs in the following:

1. The new variety flowers earlier than 'DGYPBRIDE'.

Plants of the new cultivar 'DGYPXLMU' can also be compared to the variety *Gypsophila* 'DANGYPBIGM', unpatented in the United States, protected under Plant Breeder's Rights in the European Union, Ecuador and Israel. These varieties are similar in most horticultural characteristics; however, 'DGYPXLMU' differs in the following:

1. The new variety flowers earlier than 'DANGYPBIGM'.

BRIEF DESCRIPTION OF THE PHOTOGRAPHS

Figure 1:
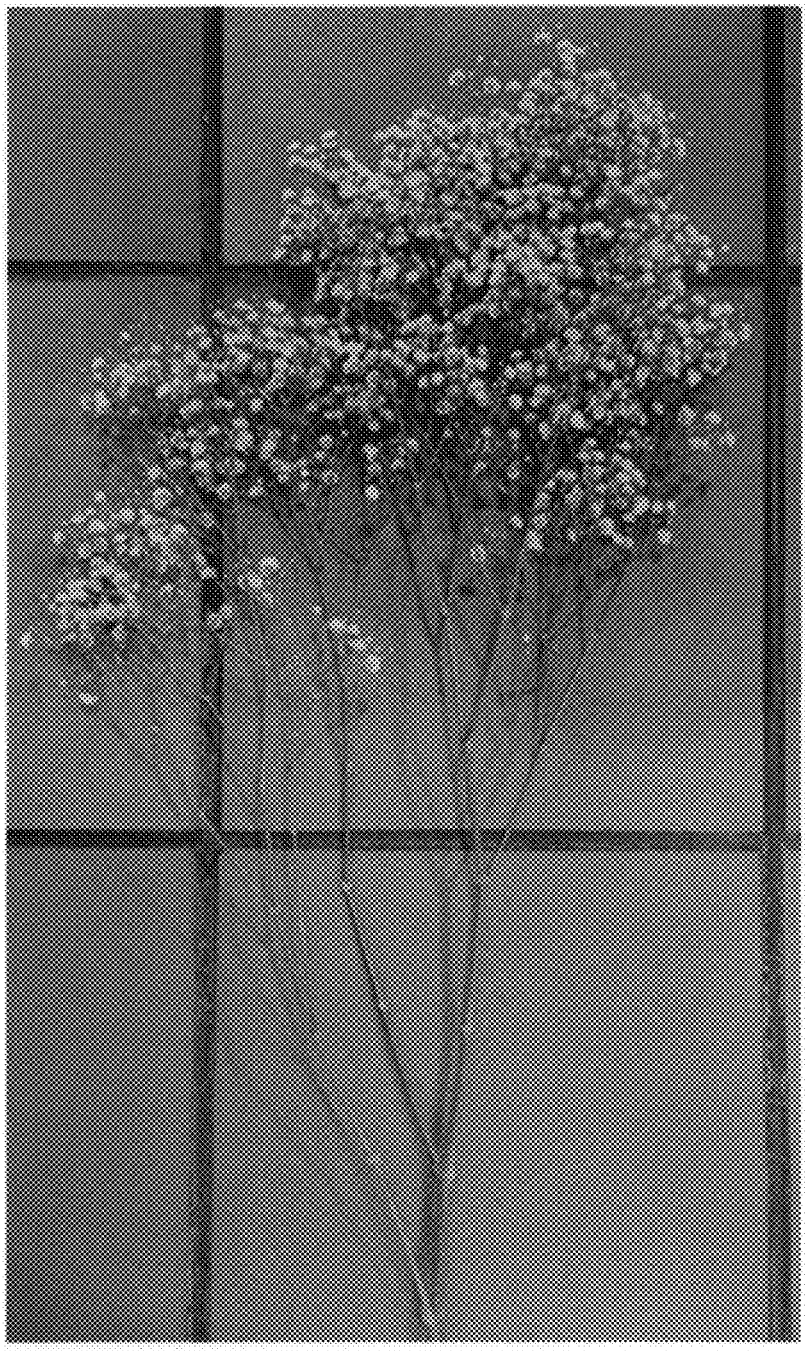

The accompanying photograph in FIG. 1 illustrates in full color a flowering stem of 'DGYPXLMU' grown outdoors in Ecuador.

Figure 2:
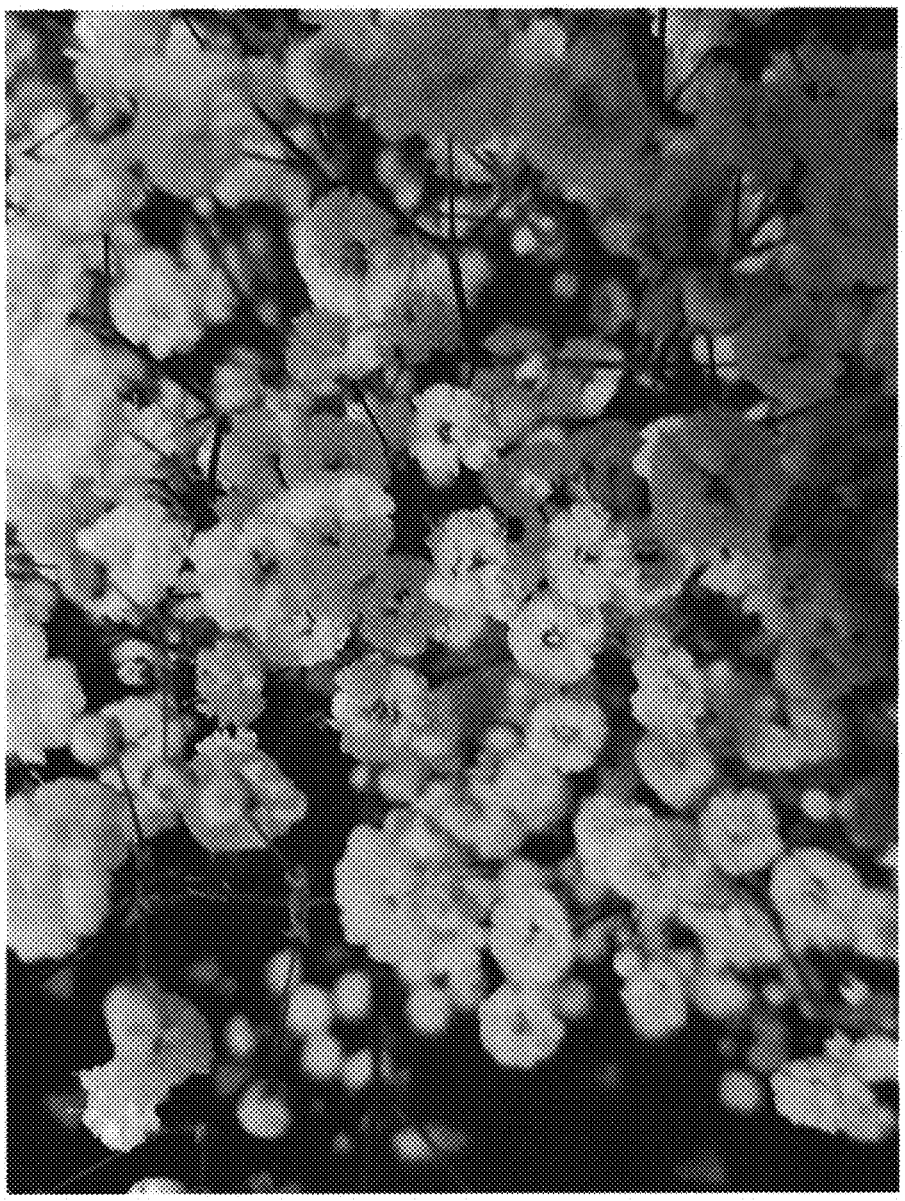

FIG. 2 illustrates in full color a close up view of flowers of 'DGYPXLMU'.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2005 except where general terms of ordinary dictionary significance are used. The following observations and measurements describe 'DGYPXLMU' plants grown in ground beds, outdoors in Ecuador under natural lighting. Measurements were taken during March of 2017. The plants were approximately 3.5 months old. The growing temperature ranged from approximately 12° C. to 25° C. day and night. Measurements and numerical values represent averages of typical plant types.

Botanical classification: *Gypsophila paniculata* 'DGYPXLMU'.

PROPAGATION

Typical propagation material: Vegetative cuttings.
Time to rooting: 21 to 28 days at approximately 20° C.
Root description: White to tan, very fibrous. Color not accurately measured with R.H.S. Colour Chart.

PLANT

Growth habit: Very upright.
Height: Approximately 100 cm.
Plant spread: Approximately 40 cm.
Branching characteristics: Basal branch and side branches along the main branch.
Length of lateral branches: Approximately 65 cm.
Approximate quantity of lateral branches: Approximately 10.
Diameter of lateral branches: Approximately 0.4 cm.
Texture of lateral branches: Smooth.
Lateral branch shape: Moderate upward curvature.
Lateral branch strength: Strong and flexible.
Lateral branch color: Approximately Yellow-Green 146C.
Internode length: 5 cm (measured at center of the stem).
Number of leaves per lateral branch: Average 40.
Age of plant described: Approximately 3.5 months.

FOLIAGE

Leaf:
- *Arrangement*.—Opposite.
- *Compound or single*.—Compound.
- *Shape of blade*.—Lanceolate.
- *Average length*.—Approximately 8 cm.
- *Average width*.—Approximately 2.5 cm.
- *Apex*.—Acuminate to Acute.
- *Base*.—Cuneate to truncate.
- *Attachment*.—Sessile.
- *Margin*.—Entire.
- *Texture of top surface*.—Rough.
- *Texture of bottom surface*.—Rough.
- *Color*.—Young foliage upper side: Near RHS Yellow-Green 147A. Young foliage under side: Near RHS Yellow-Green 147A. Mature foliage upper side: Near RHS Yellow-Green 147A. Mature foliage under side: Near RHS Yellow-Green 147A.
- *Venation*.—Type: Parallel. Venation color upper side: RHS Yellow-Green 147A. Venation color under side: Near RHS Yellow-Green 147A.

FLOWER

Bloom period:
- *Natural season*.—Spring to Summer under Ecuadorian conditions.
- *If applicable greenhouse production*.—Approximately 14 weeks.

Inflorescence:
- *Type*.—Thyres.
- *Height*.—Approximately 90 cm.
- *Width*.—Approximately 65 cm.
- *Quantity of flowers per inflorescence/umbel*.—Approximately 2000.

Bud:
- *Bud shape*.—Oblate.
- *Bud length*.—Approximately 0.1 cm.
- *Bud diameter*.—Approximately 0.2 cm.
- *Bud color*.—Base near RHS Green 137A; upper section White 155B.

Individual flower:
- *Shape*.—Rounded.
- *Quantity of flowers and buds per plant*.—Approximately 29,000.
- *Diameter of entire flower*.—Approximately 0.9 cm.
- *Depth of flower*.—Approximately 0.5 cm.
- *Rate of opening*.—Individual flowers: Fully open approximately 4 days from the bud stage.
- *Cut flower, longevity in vase*.—Approximately 10 days.
- *Flower longevity on plant*.—About 4-6 weeks.
- *Persistent or self-cleaning*.—Persistent.
- *Fragrance*.—Moderate.

Petals:
- *Length of petal*.—Approximately 0.6 cm.
- *Width of petal*.—Approximately 0.25 cm.
- *Apex*.—Blunt.
- *Shape of petal*.—Spatulate.
- *Petal margin*.—Entire.
- *Petal arrangement*.—Rosette.
- *Petal number*.—~28.
- *Petals fused*.—Only at the base.
- *Petal appearance*.—Matte.
- *Petal texture*.—Smooth, all surfaces.

Color:
- *Upper surface at first opening*.—Near RHS White NN155B.
- *Upper surface at maturity*.—Near RHS White NN155C.
- *Upper surface at fading*.—Near RHS White NN155C.
- *Under surface at first opening*.—Near RHS White NN155B.
- *Under surface at maturity*.—Near RHS White NN155C.
- *Under surface at fading*.—Near RHS White NN155C.

Petaloids or other floral structures: No.

SEPAL

Number: 5.
Sepal arrangement: Two-Layers.
Sepal length: Approximately 1 mm.
Sepal width: Approximately 0.5 mm.
Sepal shape: Lanceolate.

Sepal texture, both sides: Glabrous.
Base: Acute.
Apex shape: Acuminate to apiculate.
Margin: Entire.
Color, upper and lower: RHS Green 137B along margins, interior White 155B.

PEDUNCLE

Present: Yes.
Length: Approximately 7 cm.
Diameter: Approximately 0.1 cm.
Angle: About 15 to 35 degrees.
Strength: Strong flexible.
Texture: Glabrous.
Color: Near RHS Yellow-Green 146C.

PEDICEL

Present: Yes.
Length: Approximately 1 cm.
Diameter: Approximately 0.5 cm.
Angle: About 15 degrees from center.
Strength: Strong.
Color: Near RHS Yellow-Green 146C.

REPRODUCTIVE ORGANS

Number of pistils per flower: 2.
*Pistil length*.—Approximately 0.3 cm.
*Stigma shape*.—Can't be seen.
*Style color*.—Near RHS White 155C.
*Style length*.—Approximately 3 mm.
*Ovary color*.—Near RHS Yellow-Green N144C (upper section small flush near Purple N79A).
*Stamens quantity*.—2 to 5.
*Stamen length*.—3 mm.
*Anther shape*.—Ovoid.
*Anther length*.—1 mm.
*Anther color*.—Near RHS White 155C.
*Pollen color*.—Near RHS Yellow-Orange 23B.
*Pollen quantity*.—Scant.

OTHER CHARACTERISTICS

Fruit/seed production: Kidney-shaped, Near Brown N200A Minute, less than 1 mm.
Disease/pest resistance: Neither resistant nor susceptibility to normal diseases and pests of *Gypsophila* has been observed.
Drought tolerance and cold tolerance: Quite good as common to *Gypsophila*.
Temperature tolerance: USDA zones 3-9.

What is claimed is:

1. A new and distinct cultivar of *Gypsophila* plant named 'DGYPXLMU' as herein illustrated and described.

* * * * *